US012626340B2

(12) United States Patent
Pang et al.

(10) Patent No.: US 12,626,340 B2
(45) Date of Patent: May 12, 2026

(54) SYSTEMS, METHODS, AND APPARATUSES FOR IMPLEMENTING SELF-SUPERVISED VISUAL REPRESENTATION LEARNING USING ORDER AND APPEARANCE RECOVERY ON A VISION TRANSFORMER

(71) Applicant: Arizona Board of Regents on behalf of Arizona State University, Scottsdale, AZ (US)

(72) Inventors: Jiaxuan Pang, Mesa, AZ (US); DongAo Ma, Mesa, AZ (US); Jianming Liang, Scottsdale, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 490 days.

(21) Appl. No.: 18/126,317

(22) Filed: Mar. 24, 2023

(65) Prior Publication Data

US 2023/0306562 A1     Sep. 28, 2023

Related U.S. Application Data

(60) Provisional application No. 63/323,986, filed on Mar. 25, 2022.

(51) Int. Cl.
G06K 9/00 (2022.01)
G06T 5/10 (2006.01)
(Continued)

(52) U.S. Cl.
CPC ................. G06T 5/77 (2024.01); G06T 5/10 (2013.01); G06T 7/0012 (2013.01); G16H 30/40 (2018.01);
(Continued)

(58) Field of Classification Search
None
See application file for complete search history.

(56) References Cited

U.S. PATENT DOCUMENTS

| | | | |
|---|---|---|---|
| 2022/0198254 A1* | 6/2022 | Dalli | G06N 3/084 |
| 2023/0005251 A1* | 1/2023 | Take | G06N 20/00 |

OTHER PUBLICATIONS

Bao, H., Dong, L., Piao, S., & Wei, F. (2021). Beit: Bert pre-training of image transformers. arXiv preprint arXiv:2106.08254.
(Continued)

*Primary Examiner* — Wei Wen Yang
(74) *Attorney, Agent, or Firm* — Elliott, Ostrander & Preston, P.C.

(57) ABSTRACT

Described herein are means for performing self-supervised visual representation learning using order and appearance recovery on a vision transformer. An exemplary system having a processor and memory is specially configured to execute instructions including: receiving medical image training data; selecting a medical image; generating a first perturbed image by applying local pixel shuffling and other image perturbations and outputting a first patchified perturbed image; generating a second randomized patchified image by patchifying and applying a random permutation to the original image; inputting the first patchified perturbed image and the second randomized patchified image into first and second transformer encoders which each generate and then share first and second generated weights through the recovery of both and patch order appearance from each image; and outputting a pre-trained AI model to perform medical image diagnosis on a new medical image absent from the training data input received by the system.

20 Claims, 15 Drawing Sheets

(51) Int. Cl.
    *G06T 5/77*        (2024.01)
    *G06T 7/00*        (2017.01)
    *G16H 30/40*      (2018.01)
    *G16H 50/20*      (2018.01)
(52) U.S. Cl.
    CPC ... *G16H 50/20* (2018.01); *G06T 2207/20021* (2013.01); *G06T 2207/20032* (2013.01); *G06T 2207/20048* (2013.01); *G06T 2207/20081* (2013.01); *G06T 2207/20084* (2013.01); *G06T 2207/20092* (2013.01); *G06T 2207/20192* (2013.01); *G06T 2207/30004* (2013.01)

(56)          References Cited

OTHER PUBLICATIONS

Caron, M., Touvron, H., Misra, I., Jégou, H., Mairal, J., Bojanowski, P., & Joulin, A. (2021). Emerging properties in self-supervised vision transformers. In Proceedings of the IEEE/CVF international conference on computer vision (pp. 9650-9660).

Chen, X., Xie, S., & He, K. (2021). An empirical study of training self-supervised vision transformers. In Proceedings of the IEEE/CVF international conference on computer vision (pp. 9640-9649).

Dosovitskiy, A., Beyer, L., Kolesnikov, A., Weissenborn, D., Zhai, X., Unterthiner, T., . . . & Houlsby, N. (2020). An image is worth 16×16 words: Transformers for image recognition at scale. arXiv preprint arXiv:2010.11929.

He, K., Chen, X., Xie, S., Li, Y., Dollár, P., & Girshick, R. (2022). Masked autoencoders are scalable vision learners. In Proceedings of the IEEE/CVF conference on computer vision and pattern recognition (pp. 16000-16009).

Irvin, J., Rajpurkar, P., Ko, M., Yu, Y., Ciurea-Ilcus, S., Chute, C., . . . & Ng, A. Y. (2019, July). Chexpert: A large chest radiograph dataset with uncertainty labels and expert comparison. In Proceedings of the AAAI conference on artificial intelligence (vol. 33, No. 01, pp. 590-597).

Liu, Z., Lin, Y., Cao, Y., Hu, H., Wei, Y., Zhang, Z., . . . & Guo, B. (2021). Swin transformer: Hierarchical vision transformer using shifted windows. In Proceedings of the IEEE/CVF international conference on computer vision (pp. 10012-10022).

Nakashima, K., Kataoka, H., Matsumoto, A., Iwata, K., & Inoue, N. (2021). Can Vision Transformers Learn without Natural Images?. arXiv e-prints, arXiv-2103.

Russakovsky, O., Deng, J., Su, H., Krause, J., Satheesh, S., Ma, S., . . . & Fei-Fei, L. (2015). Imagenet large scale visual recognition challenge. International journal of computer vision, 115, 211-252.

Wang, X., Peng, Y., Lu, L., Lu, Z., Bagheri, M., & Summers, R. M. (2017). Chestx-ray8: Hospital-scale chest x-ray database and benchmarks on weakly-supervised classification and localization of common thorax diseases. In Proceedings of the IEEE conference on computer vision and pattern recognition (pp. 2097-2106).

Xie, Z., Lin, Y., Yao, Z., Zhang, Z., Dai, Q., Cao, Y., & Hu, H. (2021). Self-supervised learning with swin transformers. arXiv preprint arXiv:2105.04553.

Xie, Z., Zhang, Z., Cao, Y., Lin, Y., Bao, J., Yao, Z., . . . & Hu, H. (2022). Simmim: A simple framework for masked image modeling. In Proceedings of the IEEE/CVF conference on computer vision and pattern recognition (pp. 9653-9663).

Zhou, Zongwei, et al. "Models genesis." Medical image analysis 67 (2021): 101840.

\* cited by examiner

To Transformer Encoder
at Figure 2B.
255A

220
Patchify

215
In / Out
Painting

210
Non
Linear

202

Table 1 - 301

| Pre-Training Method | Fine-Tune on NIH ChestX-ray14 |
|---|---|
| Scratch | 70.84% ± 0.19% |
| Supervised ImageNet-21k | 75.04% ± 4.81% |
| Supervised ImageNet-21k → CheXpert | 78.87% ± 0.30% |
| MoCo v3 | 79.36% ± 0.33% |
| Fractal: ViT-Tiny | 75.14% ± 5.14% |
| DINO | 78.37% ± 0.47% |
| BEiT | 74.69% ± 0.39% |
| BEiT → ImageNet21k | 77.83% ± 2.71% |
| Masked Autoencoders | 78.97% ± 0.65% |
| Disclosed Methodology | 79.58% ± 0.13% |

FIG. 3A

Table 2 - 302

| Pre-Training Method | Fine-Tune on CheXpert |
|---|---|
| Scratch | 80.78% ± 0.13% |
| Supervised ImageNet-21k | 85.49% ± 2.61% |
| Supervised ImageNet-21k → NIH ChestX-Ray 14 | 88.16% ± 0.3% |
| Fractal: ViT-Tiny | 86.22% ± 3.11% |
| BEiT | 85.81% ± 1.00% |
| BEiT → ImageNet21k | 87.82% ± 0.28% |
| Masked Autoencoders | 87.98% ± 0.5% |
| Disclosed Methodology | 87.68% ± 0.24% |

FIG. 3B

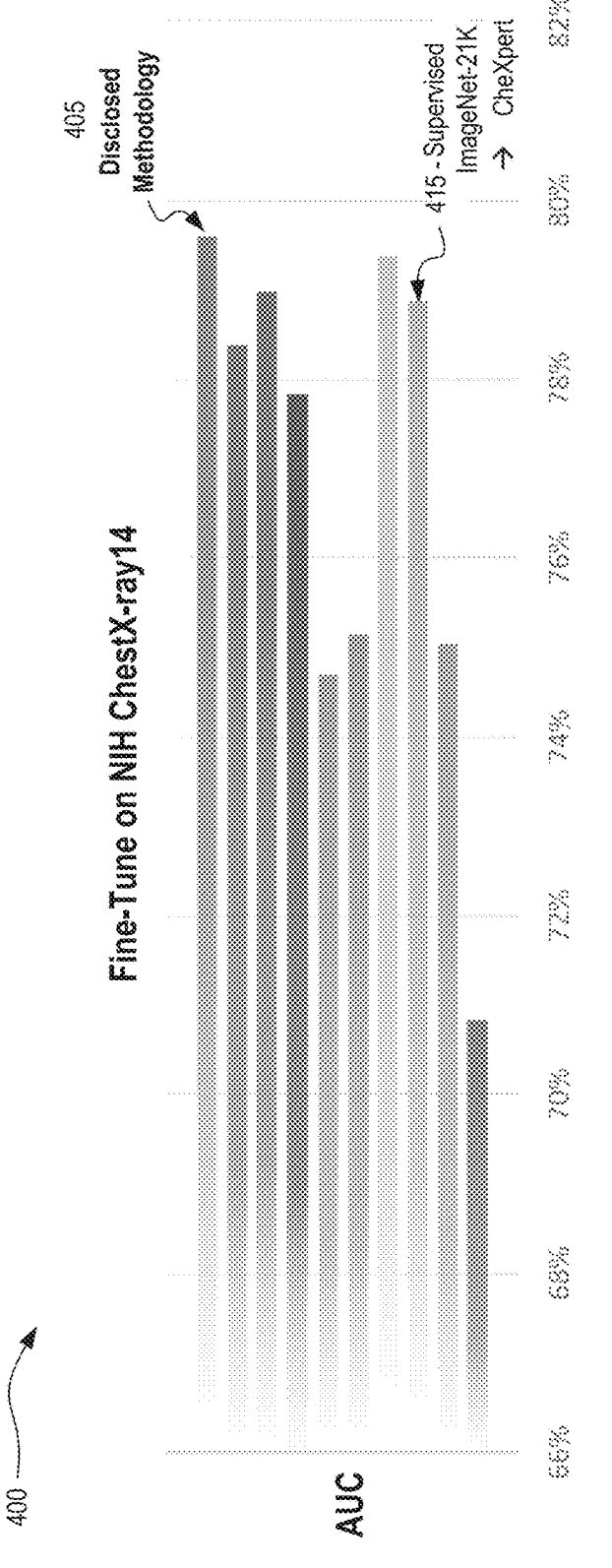
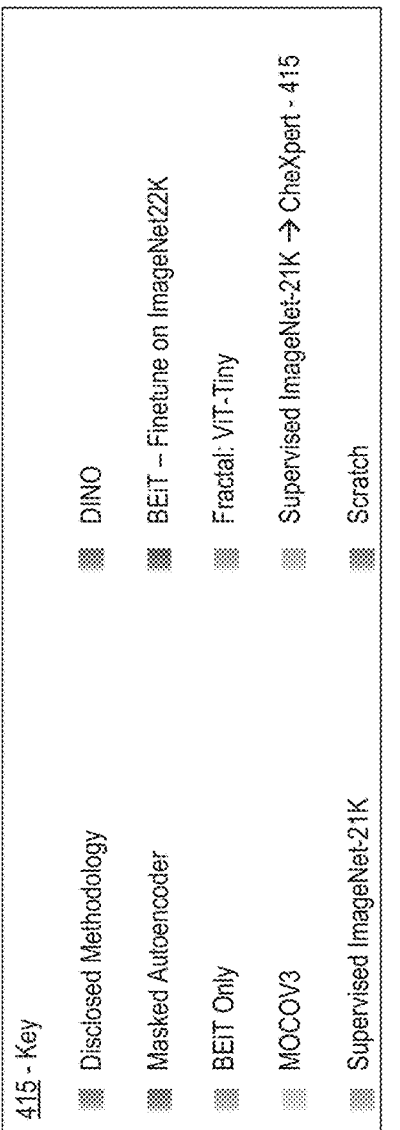
FIG. 4A

420 – RESULT 2: Disclosed methodology outperforms all transformer based self-supervised pretraining methods.

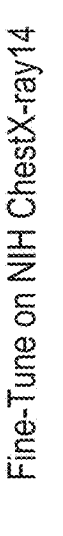

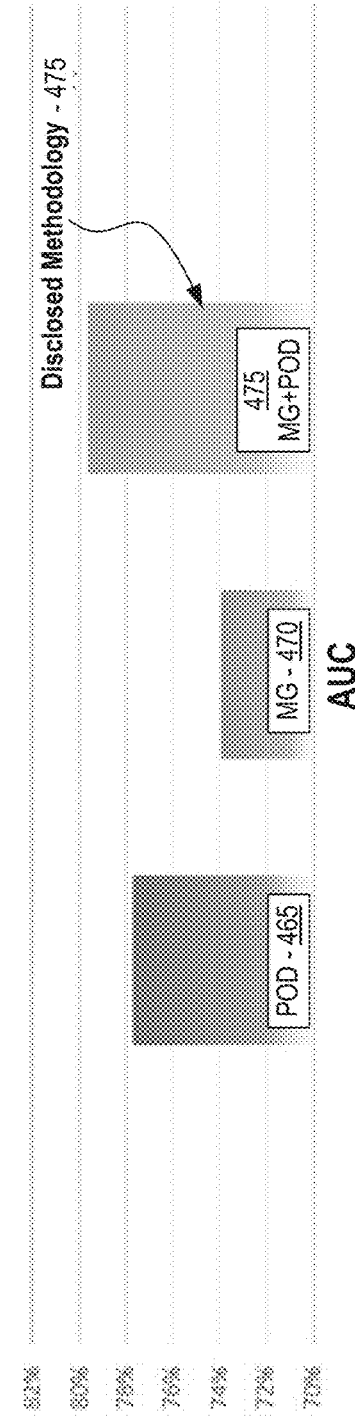

402

| Pre-Training Method | Fine-Tune on NIH ChestX-ray14 |
|---|---|
| Scratch | 70.84% ± 0.19% |
| Patch Order Prediction Only | 77.66% ± 0.24% |
| Models Genesis Restoration Only | 73.82% ± 0.32% |
| Disclosed Methodology (MG + POD) | 79.58% ± 0.13% |

Fine-Tune on NIH ChestX-ray14

Disclosed Methodology ~ 475

475
MG+POD

MG - 470

POD - 465

AUC

450 - RESULT 3: Both Models Genesis (MG) restoration and patch order prediction
(POD) provide a performance boost, with the POD providing more benefit.

FIG. 4C

Table 2 - 501

| Pre-Training Method | Fine-Tune on NIH ChestX-ray14 |
|---|---|
| 555 - Disclosed Methodology (Shallow Decoder) | 78.12% ± 0.16% |
| 560 - Disclosed Methodology (Deeper Decoder) | 79.58% ± 0.13% |

590 - RESULT 4: Pre-Training using a deeper decoder yields a higher performance jump.

FIG. 5

601

FIG. 6A

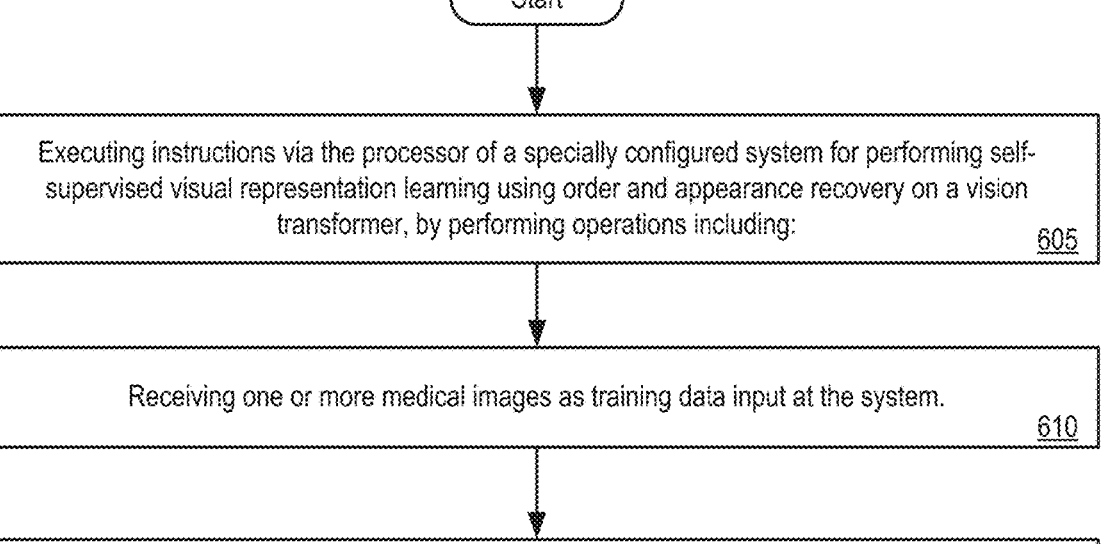

Start

Executing instructions via the processor of a specially configured system for performing self-supervised visual representation learning using order and appearance recovery on a vision transformer, by performing operations including:  605

Receiving one or more medical images as training data input at the system.  610

Selecting a medical image from among the training data input for use with performing the self-supervised visual representation learning via the system.  615

Generating a first perturbed image from the medical image selected by applying local pixel shuffling to the medical image to generate a shuffled image, applying one or more additional image perturbations to the shuffled image, to generate an interim perturbed image, transforming the interim perturbed image into a first group of patches collectively corresponding to the interim perturbed image, and outputting the first group of patches as the first perturbed image.  620

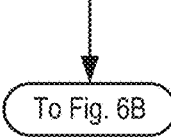

To Fig. 6B

602

FIG. 6B

( From Fig. 6A )

Generating a second perturbed image from the medical image selected by transforming the medical image selected into a second group of patches collectively corresponding to the medical image selected, applying a random permutation to the second group of patches to generate a patch randomized interim image, and outputting the patch randomized interim image as the second perturbed image.
630

Inputting the first perturbed image into a first transformer encoder to generate a first set of weights through the recovery of both and patch order appearance from the first perturbed image.
635

Inputting the second perturbed image into a second transformer encoder, different than the first transformer encoder, to generate a second set of weights through the recovery of both and patch order appearance from the second perturbed image.
640

Sharing the first and second sets of weights among the first and second transformer encoders.
645

Outputting a pre-trained AI model to perform medical image diagnosis on a new medical image which forms no part of the training data input received by the system.
650

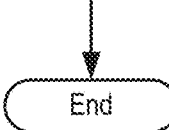
( End )

SYSTEMS, METHODS, AND APPARATUSES FOR IMPLEMENTING SELF-SUPERVISED VISUAL REPRESENTATION LEARNING USING ORDER AND APPEARANCE RECOVERY ON A VISION TRANSFORMER

CLAIM OF PRIORITY

This non-provisional U.S. Utility Patent Application is related to, and claims priority to the U.S. Provisional Patent Application No. 63/323,986, entitled "SYSTEMS, METH-ODS, AND APPARATUSES FOR IMPLEMENTING SELF-SUPERVISED VISUAL REPRESENTATION LEARNING BY RECOVERING ORDER AND APPEAR-ANCE ON VISION TRANSFORMER," filed Mar. 25, 2022, the entire contents of which is incorporated herein by reference as though set forth in full.

GOVERNMENT RIGHTS AND GOVERNMENT AGENCY SUPPORT NOTICE

This invention was made with government support under R01 HL128785 awarded by the National Institutes of Health. The government has certain rights in the invention.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

Embodiments of the invention relate generally to the field of medical imaging and analysis using self-supervised learn-ing (SSL) capabilities of a Vision Transformer (ViT) for the classification and annotation of medical images, and more particularly, to systems, methods, and apparatuses for imple-menting self-supervised visual representation learning using order and appearance recovery on a vision transformer, specifically in which trained models derived from such techniques are utilized for processing medical images.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely repre-sents different approaches, which in and of themselves may also correspond to embodiments of the claimed inventions.

Machine learning models have various applications to automatically process inputs and produce outputs consider-ing situational factors and learned information to improve output quality. One area where machine learning models, and neural networks in particular, provide high utility is in the field of processing medical images.

Within the context of machine learning and with regard to deep learning specifically, a Convolutional Neural Network (CNN, or ConvNet) is a class of deep neural networks, very often applied to analyzing visual imagery. Convolutional Neural Networks are regularized versions of multilayer perceptrons. Multilayer perceptrons are fully connected net-works, such that each neuron in one layer is connected to all neurons in the next layer, a characteristic which often leads to a problem of overfitting of the data and the need for model regularization. Convolutional Neural Networks also seek to apply model regularization, but with a distinct approach. Specifically, CNNs take advantage of the hierarchical pat-tern in data and assemble more complex patterns using smaller and simpler patterns. Consequently, on the scale of connectedness and complexity, CNNs are on the lower extreme.

Also used within the context of machine learning are Vision Transformers (ViTs). A Vision Transformer is a transformer that is targeted at vision processing tasks such as image recognition. Transformers found their initial applica-tions in natural language processing (NLP) tasks, as dem-onstrated by language models such as BERT and GPT-3. By contrast, the typical image processing system uses a convo-lutional neural network (CNN). Well-known projects include Xception, ResNet, EfficientNet, DenseNet, and Inception.

Unlike CNNs, Transformers measure the relationships between pairs of input tokens (words in the case of text strings), termed attention. The cost is exponential with the number of tokens. For images, the basic unit of analysis is the pixel. However, computing relationships for every pixel pair in a typical image is prohibitive in terms of memory and computation. Instead, ViT computes relationships among pixels in various small sections of the image (e.g., 16×16 pixels), at a drastically reduced cost. The sections (with positional embeddings) are placed in a sequence. The embeddings are learnable vectors. Each section is arranged into a linear sequence and multiplied by the embedding matrix. The result, with the position embedding is fed to the transformer. The architecture for image classification is the most common and uses only the Transformer Encoder in order to transform the various input tokens. However, there are also other applications in which the decoder part of the traditional Transformer Architecture is also used.

Heretofore, self-supervised learning has been sparsely applied in the field of medical imaging. Nevertheless, there is a massive need to provide automated analysis to medical imaging with a high degree of accuracy so as to improve diagnosis capabilities, control medical costs, and to reduce workload burdens placed upon medical professionals.

Not only is annotating medical images tedious and time-consuming, but it also demands costly, specialty-oriented expertise, which is not easily accessible.

The present state of the art may therefore benefit from the systems, methods, and apparatuses for implementing self-supervised visual representation learning using order and appearance recovery on a vision transformer, as is described herein.

BRIEF DESCRIPTION OF THE DRAWINGS

Embodiments are illustrated by way of example, and not by way of limitation, and can be more fully understood with reference to the following detailed description when con-sidered in connection with the figures in which:

FIG. 3A depicts Table 1 illustrating performance of the disclosed methodology when compared with prior known techniques, in accordance with described embodiments;

FIG. 3B depicts Table 2 illustrating performance of the disclosed methodology when compared with prior known techniques, in accordance with described embodiments;

FIGS. 4A and 4B depict charts comparing performance of the disclosed methodology with other prior known techniques, in accordance with described embodiments;

FIG. 4C depicts a chart comparing performance of the disclosed methodology with other pre-training methods, in accordance with described embodiments;

FIG. 5 depicts another result illustrating the performance of the disclosed methodology when fine-tuning on the NIH ChestX-ray14 dataset, in accordance with described embodiments;

FIGS. 6A and 6B depict a flow diagram illustrating a method for performing self-supervised visual representation learning using order and appearance recovery on a vision transformer, in accordance with disclosed embodiments;

DETAILED DESCRIPTION

Described herein are systems, methods, and apparatuses for implementing self-supervised visual representation learning using order and appearance recovery on a vision transformer, in which trained models derived from such techniques are utilized for processing medical images.

Medical imaging follows protocols for specific therapeutic purposes, resulting in consistent and recurring anatomical features across all scans, which can serve as robust, organically occurring supervisory signals, leading to more powerful models. The Vision Transformer (ViT) architecture described herein has been successfully applied to a variety of natural image computer vision (CV) tasks indicating that it holds great potential in medical image analysis.

Within the context of medical imaging analysis, there is the question of: "How can self-supervised visual representation learning be enhanced by using recurring anatomical structures and the cross-attention mechanisms?" The described Vision Transformer (ViT) architecture set forth herein, and more specifically, the techniques for self-supervised visual representation learning using order and appearance recovery on a vision transformer as described in greater detail below, address this question and overcome the shortcomings of prior known techniques.

Figure 1:
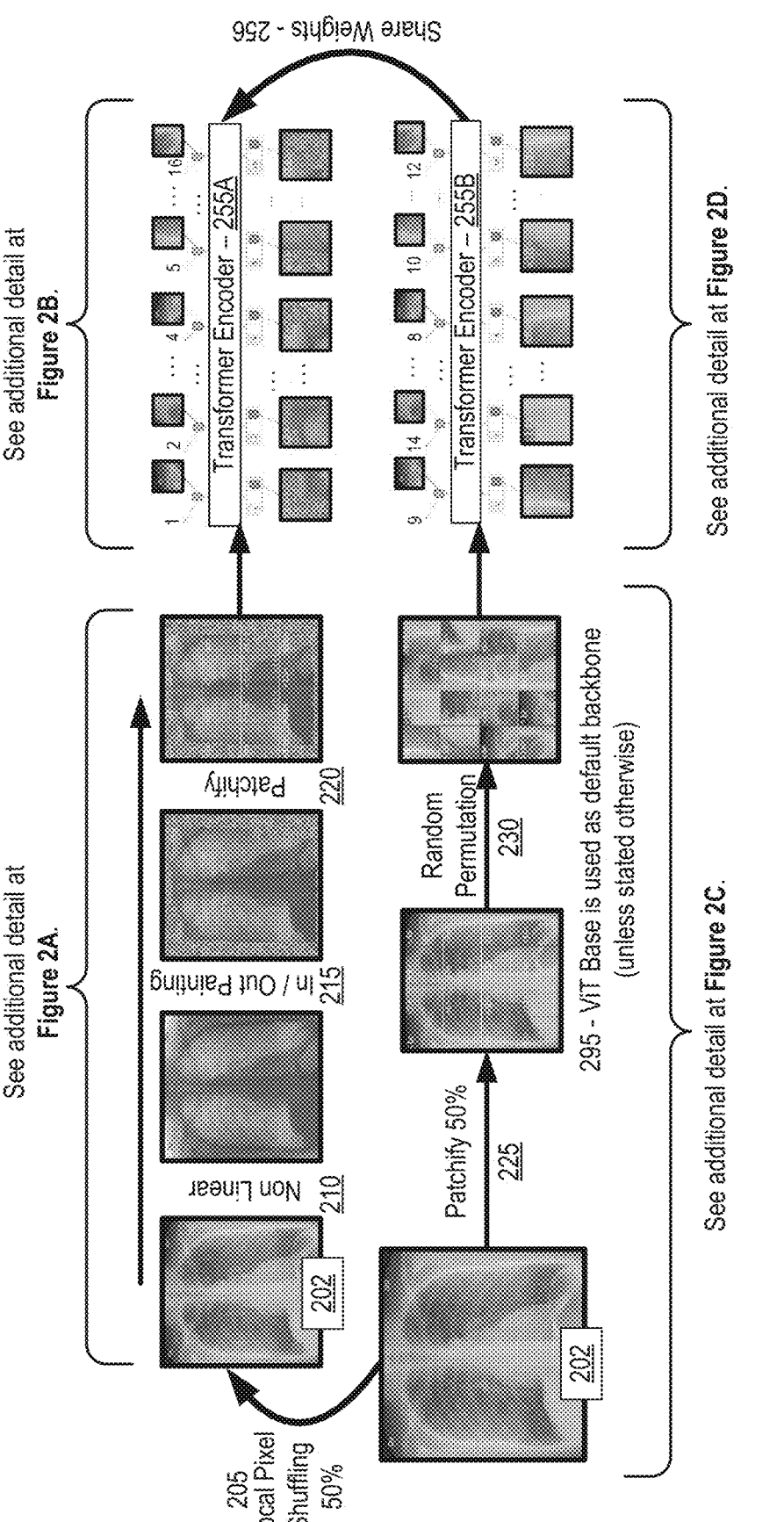
FIG. 1 depicts use of the described Vision Transformer (ViT) architecture, in accordance with described embodi-ments.

FIG. 1 depicts use of the described Vision Transformer (ViT) architecture, in accordance with described embodiments.

As shown in FIG. 1, there are various operational blocks, including local pixel shuffling of 50% at element 205, application of the ViT base as the default backbone (unless an alternate is expressly specified) as depicted at element 295, and the transformer/encoder blocks at elements 255A and 255B, which weights are shared between them, as indicated by element 256.

More particularly, the local pixel shuffling as shown here at element 205 is depicted as being applied at 50% to a medical image 202.

As shown here at the upper left section of FIG. 1, non-linear processing is applied at operation 210 to the medical image 202, and then an in-painting/out-painting operation at element 215 is applied to the medical image 202, and then the medical image 202 having been subjected to the non-linear processing operation 210 and the in-painting/out-painting operation at element 215 is then subjected to a "patchify" operation at element 220. That patchified medical image is then output from the processing and provided as input to transformer encoder 255A. More detail is provided at FIG. 2A below.

As shown here at the lower left section of FIG. 1, operation 225 separately applies a "patchify" operation of 50% to the medical image 202, and then a "random permutation" operation is applied at element 230 to the medical image having been subjected to the "patchify" algorithm. The scrambled medical image having been subjected to the random permutation operation at element 230 is then output and provided as input to the transformer encoder 255B. More detail is provided at FIG. 2B below.

As shown at the right-most section of FIG. 1, there are two transformer encoders, 255A and 255B, in which the transformer encoder 255B shares weights with transformer encoder 255A. More detail is provided at FIGS. 2B and 2C.

Generally speaking, the processing set forth at FIG. 1 applies non-linear modifications at element 210, in/out painting operations at element 215, and a "patchify" algorithm at element 220 to perturb the image. The perturbed image is then processed through a first transformer encoder 255A.

Separately, the image subjected to the local pixel shuffling at 50% at element 205 is then processed through the "patchify" algorithm at 50% at element 225 and then processed again with random permutations at element 230 to again perturb the image. The perturbed image is then processed through a second transformer encoder at element 255B, and weights are then shared amongst the two transformer encoders as depicted by element 256.

Figure 2A:
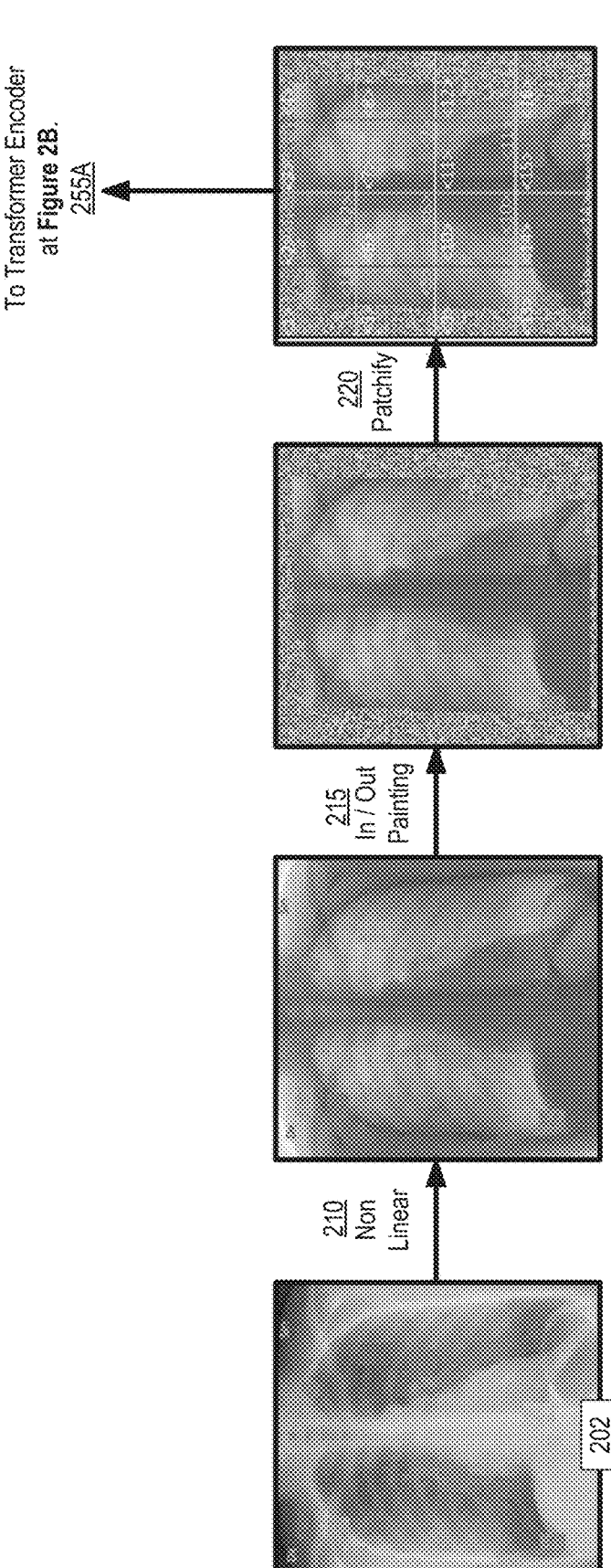
FIG. 2A depicts a subset of the described Vision Transformer (ViT) architecture, in accordance with described embodiments.

FIG. 2A depicts a subset of the described Vision Transformer (ViT) architecture in greater detail, in accordance with described embodiments.

Specifically, image manipulations are depicted here, beginning with the non-linear processing at element 210, followed by the in-painting/out painting operations at element 215, and lastly the application of the "patchify" algorithm at element 220. The resulting perturbed image is then transmitted to the transformer encoder at element 255A, which is depicted in greater detail at FIG. 2B.

In the context of image processing, linear processing type image processing methods may be applied to images to improve their smoothness or to sharpen detail boundaries. Such techniques may be either linear or nonlinear. Non-linear processing methods specifically are those in which individual data points are compared with a standard or fit to determine the suitability of those individual data points for modification or acceptance. Non-linear methods are utilized to improve an original input image by modification or removal of improbable values by rejecting data from smoothing areas because due to size disagreement or through the rejection of spatial frequency components that are too small.

A simple non-linear filter may apply a median or rank-order filtering technique, in which the median filter output depends on the ordering of input values, typically ranked from smallest to largest or vice versa. A support range for the filter with an odd number of values is used, making it easy to select the output, but other selection techniques may be applied.

Consider a filter based on five values. In the region of interest, those values are ordered from smallest to largest. The value at position 2 may be selected as the output. At low frequency, the values are likely to be the same or close to the same, in which event, the value selected will be the original value, plus or minus some small error. At high frequency, such as an edge, values on one side of the edge will be low and the values on the other side will be high. Thus, for ordering, values will remain in the low position and the high values will remain in the high position. A selection of a middle value will be forced into either the low side or the high side, and not allowed to remain in a middle position, which is contrary to that which is permissible with a linear low-pass filter. This is called edge-preserving and is helpful to remove outliers such as impulse noise.

Again, in the context of image processing, in-painting is carryover from the physical conservation process where damaged, deteriorated, or missing parts of an image are filled in to present a complete image. With its roots in physical artwork, such as painting and sculpture, traditional in-painting is performed by a trained art conservator who has carefully studied the artwork to determine the mediums and techniques used in the piece, potential risks of treatments, and ethical appropriateness of treatment. In-painting via an AI model is one tool amongst a large set of image generation techniques, with the goal of in-painting being to permit the AI model to fill the missing pixels. It can be seen as creating or modifying pixels which also includes tasks like deblurring, denoising, artifact removal, etc. Methods for solving those problems usually rely on an auto-encoder, or more specifically, a neural network that is trained to copy inputs to outputs. It is comprised of an encoder which learns a code to describe the input, h=f(x), and a decoder that produces the reconstruction, based on that function.

Similarly, in the context of image processing, out-painting also generates new pixels, but does so by extending images beyond their borders, thus generating larger images with added or extended peripheries.

Continuing within the context of image processing, "patchifying" an image or the "patchification" of an image is the splitting of the image into small overlapping or non-overlapping patches by given patch cell size, depending on the implementation needs, and then the subsequent merging of those patches into an original image, having the various patches, crops, or demarcation zones to identify the distinct patches created and their spatial relationship to one another within the original image. This pacification can be done to a default quantity of patches (e.g., such as 64 total patches on an 8×8 grid) or broken up into a user-specified non-default quantity of patches.

Figure 2B:
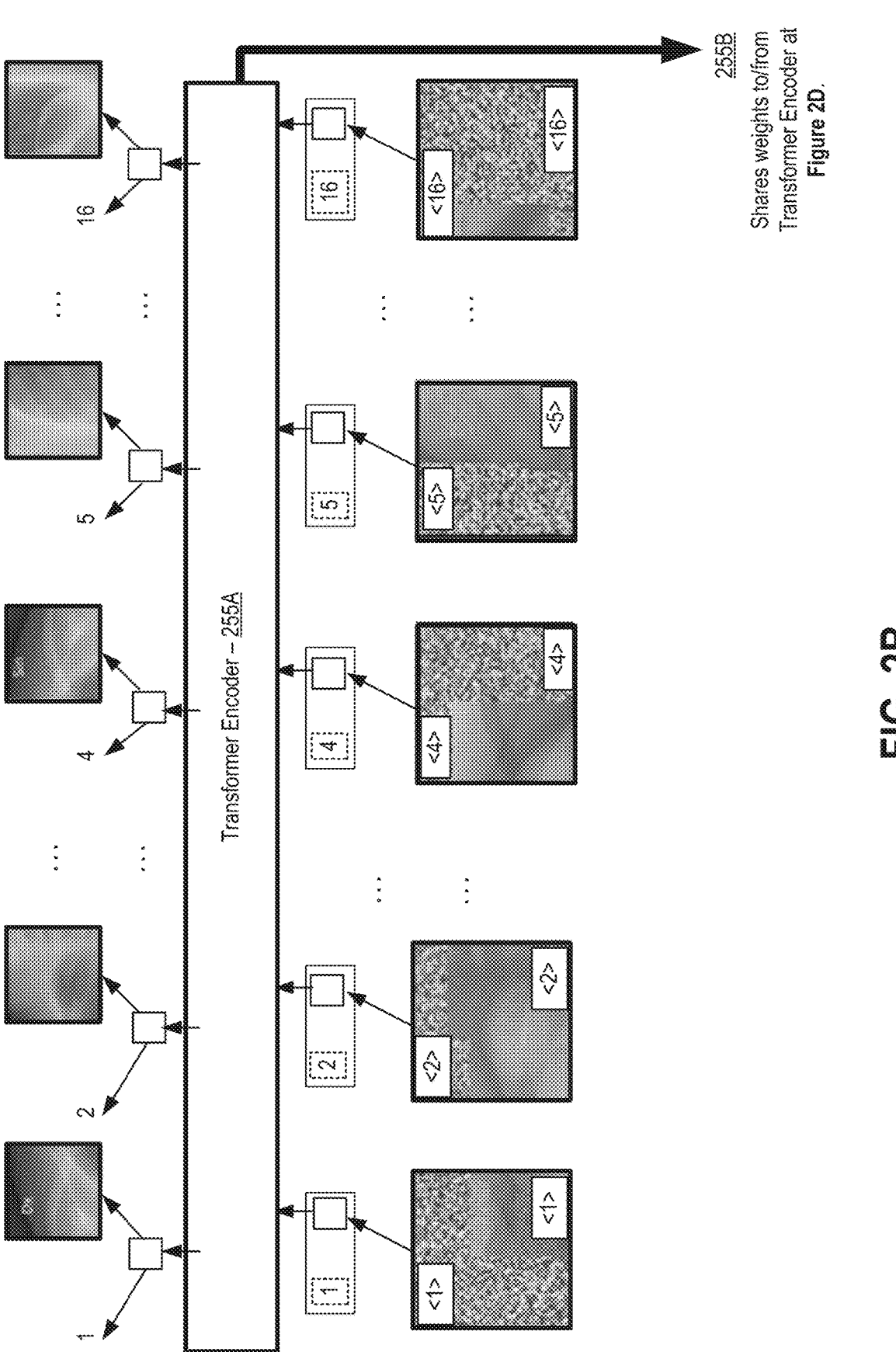
FIG. 2B depicts a subset of the described Vision Transformer (ViT) architecture, in accordance with described embodiments.

FIG. 2B depicts a subset of the described Vision Transformer (ViT) architecture in greater detail, specifically the first transformer encoder at element 255A.

As shown here, a transformer encoder 255A with multiple nodes performs additional processing on the perturbed image received. According to the depicted embodiment, self-supervised visual representation learning is implemented by recovering order and appearance information using the vision transformer encoder as shown here, which results in determined weights which are then shared with a second and separate transformer encoder at element 255B which is depicted in greater detail with reference to FIG. 2D.

Figure 2C:
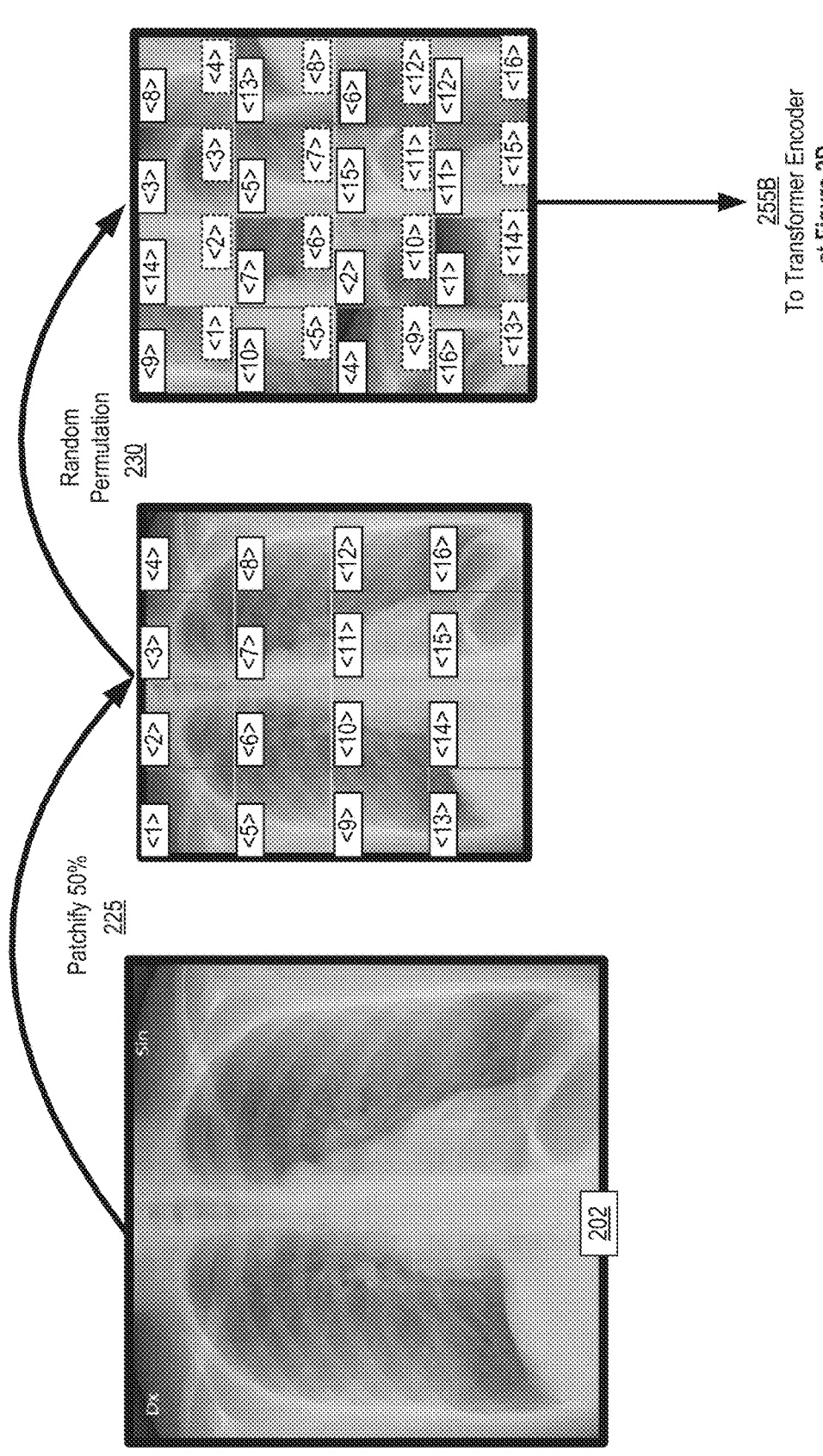
FIG. 2C depicts another subset of the described Vision Transformer (ViT) architecture, in accordance with described embodiments.

FIG. 2C depicts another subset of the described Vision Transformer (ViT) architecture in greater detail, specifically showing additional image perturbations.

As shown here, additional image manipulations are performed against the subject medical image 202, beginning with application of the "patchify" algorithm at 50% as depicted by element 225 and then followed by random permutations on the image as depicted by element 230, effectively scrambling the locations of the patches established within the medical image 220 by the "patchify" algorithm applied at element 225. The resulting perturbed image is then output from the processing and transmitted as input to the second transformer encoder 255B which is depicted in greater detail at FIG. 2D. Notably, a base model ViT is utilized as the default backbone for all operations. However, this default may be changed if specified by the user for the particular implementation.

Figure 2D:
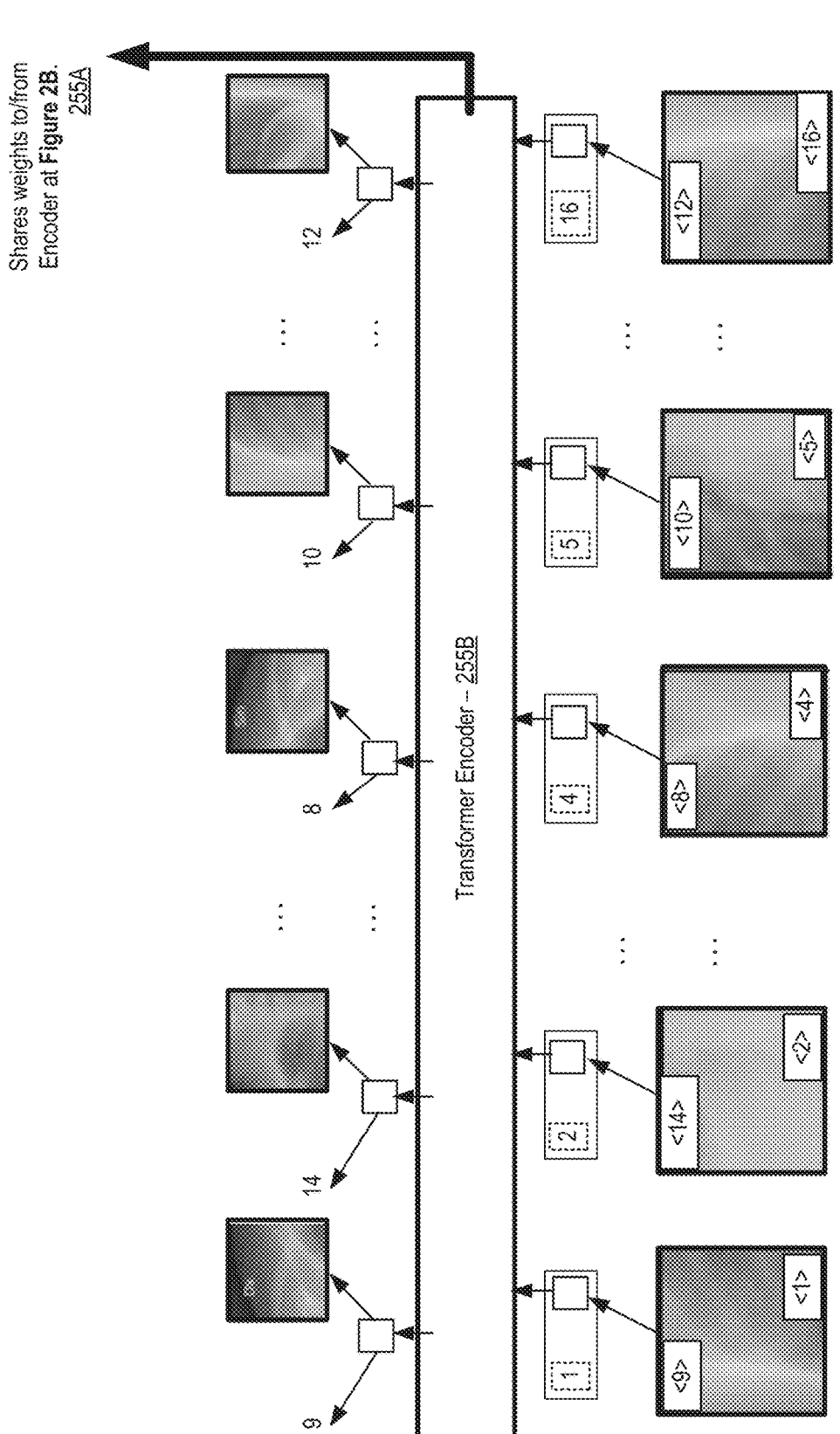
FIG. 2D depicts another subset of the described Vision Transformer (ViT) architecture, in accordance with described embodiments.

FIG. 2D depicts another subset of the described Vision Transformer (ViT) architecture in greater detail, specifically the second transformer encoder 255B.

As shown here, a second transformer encoder 255B with multiple nodes performs additional processing on the perturbed image received from the image processing performed at FIG. 2C against the subject medical image 202.

According to the depicted embodiment, self-supervised visual representation learning is again implemented by recovering order and appearance information using the vision transformer encoder as shown here, which results in determined weights which are then shared with the first transformer encoder 255A, described above and depicted in greater detail with reference to FIG. 2B.

This results in two differently and distinctly perturbed images from the original identical subject medical image 202, each of which are then subjected to similar or identical self-supervised visual representation learning through order and appearance information recovery using the two separate vision transformer encoders 255A and 255B, each of which operating independently against differently perturbed variations of the original subject medical image 202. Consequently, different weights will be determined by each of the two separate vision transformer encoders 255A and 255B, and these different weights are then shared between the two respective transformer encoders 255A and 255B.

FIG. 3A depicts Table 1 at element 301 illustrating performance of the disclosed methodology when compared with prior known techniques.

As shown here, the disclosed methodology when used as a pre-training method results in 79.58%±0.13% performance when used for fine-tuning on the NIH ChestX-ray14 dataset. As depicted, this result by the disclosed methodology out-performs all other techniques evaluated and specifically outperforms the ImageNet-21K supervised pre-training technique (see e.g., Result 1 at FIG. 4A).

FIG. 3B depicts Table 2 at element 302 illustrating performance of the disclosed methodology when compared with prior known techniques.

As shown here, the disclosed methodology when used as a pre-training method results in 87.68%±0.24% performance when used for fine-tuning on the CheXpert dataset. As depicted, this result by the disclosed methodology outperforms all transformer based self-supervised pre-training techniques evaluated (see e.g., Result 2 at FIG. 4B).

Figure 4B:
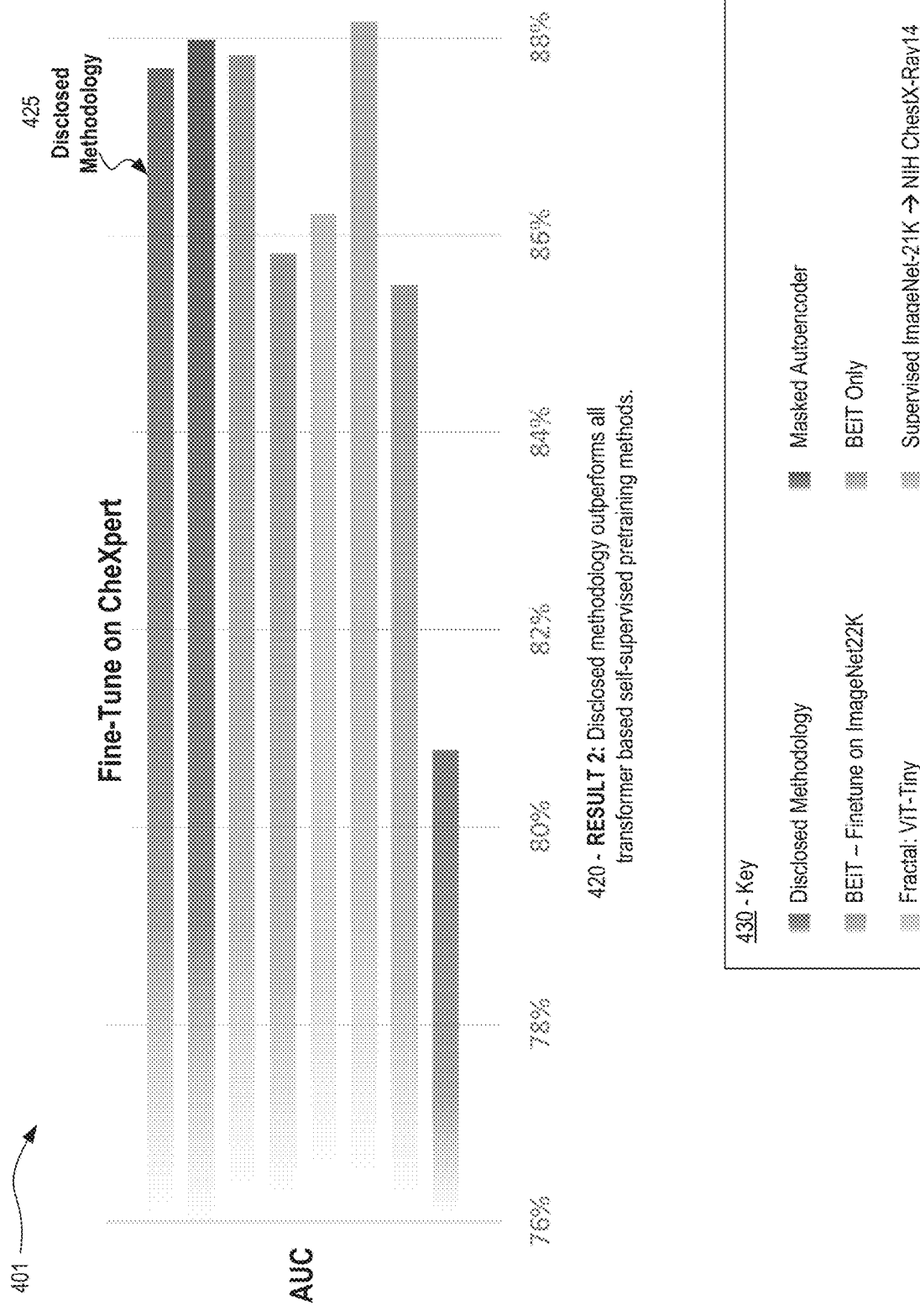

FIGS. 4A and 4B depict charts 400 and 401 comparing performance of the disclosed methodology 405 with other prior known techniques for each such technique when fine-tuned using the NIH ChestX-ray14 dataset at FIG. 4A and when fine-tuning on the CheXpert datasets at FIG. 4B. The key for FIG. 4A is set forth at element 415 and the key for FIG. 4B is set forth at element 430.

Again, as can be seen by the results depicted here, the disclosed methodology 405 out-performs all other techniques evaluated when fine-tuning on the NIH ChestX-ray14 dataset, including outperforming the ImageNet-21K supervised pre-training technique as shown by element 415 at FIG. 4A (see e.g., Result 1 at element 410, FIG. 4A). Further still, as depicted at FIG. 4B, the disclosed methodology 425 again out-performs all transformer based self-supervised pre-training techniques evaluated (see e.g., Result 2 at element 420, FIG. 4B).

FIG. 4C depicts a chart 402 comparing performance of the disclosed methodology with other pre-training methods.

As shown here, the disclosed methodology indicated as "MG+POD at element 475, representing the application of both Models Genesis (MG) and also Patch Order Prediction (POD), when used as a pre-training method for fine-tuning on the NIH ChestX-ray14 dataset results in a measured performance of 79.58%±0.13%, which exceeds each of the other methods evaluated.

Therefore, as depicted by Result 3, at element 450, FIG. 4C, both Models Genesis (MG) restoration at element 470 and patch order prediction (POD) at element 465 provide a performance boost, with the POD method 465 providing more benefit than Models Genesis (MG) restoration, and the disclosed methodology at element 475 using MG+POD at element 475, providing the greatest performance increase.

FIG. 5 depicts another result illustrating the performance of the disclosed methodology when fine-tuning on the NIH ChestX-ray14 dataset.

As is shown here, when the disclosed methodology with a shallow decoder is used (see element 555) as the pre-training method for fine-tuning on the NIH ChestX-ray14 dataset, a resulting performance of 79.12%±0.16% is attained. Conversely, when the disclosed methodology with a deeper decoder is used (see element 560) as the pre-training method for fine-tuning on the NIH ChestX-ray14 dataset, a resulting performance of 79.58%±0.13% is attained.

Therefore, as depicted by Result 4, at element 590, FIG. 5, pre-training using a deeper decoder yields a higher performance jump, and thus, the greatest performance increase.

FIGS. 6A and 6B depict a flow diagram illustrating a method 601-602 for performing self-supervised visual representation learning using order and appearance recovery on a vision transformer, in accordance with disclosed embodiments. Method 601-602 may be performed by processing logic that may include hardware (e.g., circuitry, dedicated logic, programmable logic, microcode, etc.), software (e.g., instructions run on a processing device) to perform various operations such as designing, defining, retrieving, parsing, persisting, exposing, loading, executing, operating, receiving, generating, storing, maintaining, creating, returning, presenting, interfacing, communicating, transmitting, querying, processing, providing, determining, triggering, displaying, updating, sending, etc., in pursuance of the systems and methods as described herein. For example, the system 701 (see FIG. 7) and the machine 801 (see FIG. 8) and the other supporting systems and components as described herein may implement the described methodologies. Some of the blocks and/or operations listed below are optional in accordance with certain embodiments. The numbering of the blocks presented is for the sake of clarity and is not intended to prescribe an order of operations in which the various blocks must occur.

With reference to the method 601-602 depicted at FIGS. 6A and 6B, starting at block 605, there is a method performed by executing instructions via the processor of a specially configured system for performing self-supervised visual representation learning using order and appearance recovery on a vision transformer. Such a system may be configured with at least a processor and a memory to execute specialized instructions which cause the system to perform the following operations:

At block 610, processing logic receives one or more medical images as training data input at the system.

At block 615, processing logic selects a medical image from among the training data input for use with performing the self-supervised visual representation learning via the system.

At block 620, processing logic generates a first perturbed image from the medical image selected by applying local pixel shuffling to the medical image to generate a shuffled image, applying one or more additional image perturbations to the shuffled image, to generate an interim perturbed image, transforming the interim perturbed image into a first group of patches collectively corresponding to the interim perturbed image, and outputting the first group of patches as the first perturbed image.

Transitioning from FIG. 6A to the processing which continues at FIG. 6B, the processing of method 601-602 resumes at block 630.

At block 630, processing logic generates a second perturbed image from the medical image selected by transforming the medical image selected into a second group of patches collectively corresponding to the medical image selected, applying a random permutation to the second group of patches to generate a patch randomized interim image, and outputting the patch randomized interim image as the second perturbed image.

At block 635, processing logic inputs the first perturbed image into a first transformer encoder to generate a first set of weights through the recovery of both and patch order appearance from the first perturbed image.

At block 640, processing logic inputs the second perturbed image into a second transformer encoder, different than the first transformer encoder, to generate a second set of weights through the recovery of both and patch order appearance from the second perturbed image.

At block 645, processing logic shares the first and second sets of weights among the first and second transformer encoders.

At block 650, processing logic outputs a pre-trained AI model to perform medical image diagnosis on a new medical image which forms no part of the training data input received by the system.

According to another embodiment, method 601-602 further includes: applying fine-tuning to the pre-trained AI model using a publically available standardized dataset.

According to another embodiment, method 601-602 further includes: outputting the pre-trained and fined-tuned AI model to perform the medical image diagnosis.

According to another embodiment of method 601-602, applying the fine-tuning to the pre-trained AI model using the publically available standardized dataset includes using one of a publically available standardized NIH ChestX-ray14 dataset or a publically available standardized CheX-pert dataset.

According to another embodiment of method 601-602, applying the one or more additional image perturbations to the shuffled image includes applying non-linear processing to the shuffled image to generate a processed shuffled image.

According to another embodiment of method 601-602, applying the one or more additional image perturbations to the shuffled image includes applying in-painting or out-painting or both in-painting and out-painting to the pro-cessed shuffled image to generate an expanded image.

According to another embodiment of method 601-602, transforming the interim perturbed image into the first group of patches collectively corresponding to the interim per-turbed image includes transforming the expanded image into the first group of patches collectively corresponding to the expanded image generated from the application of the in-painting or out-painting or both.

According to another embodiment of method 601-602, a Vision Transformer (ViT) base model is utilized as a default backbone for applying the first and second image perturba-tions of the medical image.

According to another embodiment of method 601-602, a user-specified Vision Transformer (ViT) model is specified as a second input and the method further includes supple-menting a Vision Transformer (ViT) base model utilized as a default backbone with the user-specified Vision Trans-former (ViT) model specified as the second input.

According to another embodiment, the method 601-602 further includes: applying the first and second image per-turbations of the medical image utilizing the user-specified Vision Transformer (ViT) model as specified via the second input.

According to another embodiment of method 601-602, applying the local pixel shuffling to the medical image to generate the shuffled image includes applying the local pixel shuffling at a 50% application threshold to generate the shuffled image.

According to another embodiment of method 601-602, transforming the interim perturbed image into a first group of patches collectively corresponding to the interim per-turbed image, and outputting the first group of patches as the first perturbed image includes executing instructions via the processor for applying a patchify algorithm to the interim perturbed image to generate the first perturbed image.

According to another embodiment of method 601-602, transforming the interim perturbed image into a first group of patches collectively corresponding to the interim per-turbed image includes, dividing the interim perturbed image into a 4×4 block of 16 total patches or into an 8×8 block of 64 total patches.

According to another embodiment, the method 601-602 further includes: outputting the 4×4 block of 16 total patches or the 8×8 block of 64 total patches as the first perturbed image.

According to another embodiment of method 601-602, generating the first perturbed image from the medical image and generating the second perturbed image from the medical image includes executing a Vision Transformer (ViT) at the system against the medical image selected to generate the first and second perturbed images.

According to a particular embodiment, there is a non-transitory computer-readable storage media having instructions stored thereupon that, when executed by a system having at least a processor and a memory therein, the instructions cause the processor to execute instructions for performing self-supervised visual representation learning using order and appearance recovery on a vision trans-former, by performing operations including: receiving one or more medical images as training data input at the system; selecting a medical image from among the training data input for use with performing the self-supervised visual representation learning via the system; generating a first perturbed image from the medical image selected by apply-ing local pixel shuffling to the medical image to generate a shuffled image, applying one or more additional image perturbations to the shuffled image, to generate an interim perturbed image, transforming the interim perturbed image into a first group of patches collectively corresponding to the interim perturbed image, and outputting the first group of patches as the first perturbed image; generating a second perturbed image from the medical image selected by trans-forming the medical image selected into a second group of patches collectively corresponding to the medical image selected, applying a random permutation to the second group of patches to generate a patch randomized interim image, and outputting the patch randomized interim image as the second perturbed image; inputting the first perturbed image into a first transformer encoder to generate a first set of weights through the recovery of both and patch order appearance from the first perturbed image; inputting the second perturbed image into a second transformer encoder, different than the first transformer encoder, to generate a second set of weights through the recovery of both and patch order appearance from the second perturbed image; sharing the first and second sets of weights among the first and second transformer encoders; and outputting a pre-trained AI model to perform medical image diagnosis on a new medical image which forms no part of the training data input received by the system.

Figure 7:
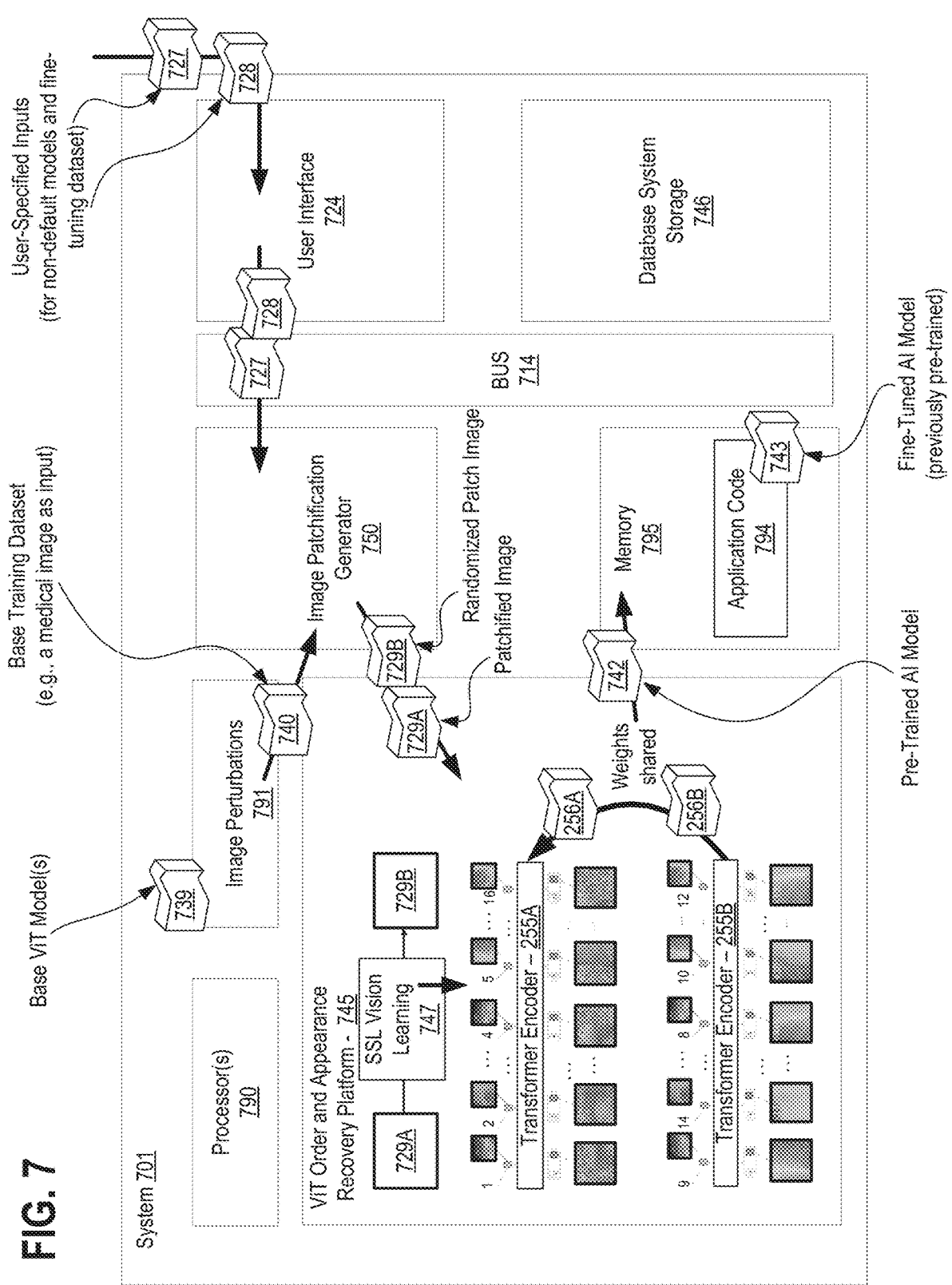
FIG. 7 shows a diagrammatic representation of a system within which embodiments may operate, be installed, integrated, or configured, in accordance with one embodiment.

FIG. 7 shows a diagrammatic representation of a system 701 within which embodiments may operate, be installed, integrated, or configured. In accordance with one embodi-ment, there is a system 701 having at least a processor 790 and a memory 795 therein to execute implementing appli-cation code 794. Such a system 701 may communicatively interface with and cooperatively execute with the benefit of remote systems, such as a user device sending instructions and data via user interface 724, a user device to receive as an output from the system 701 via user interface 724, or systems within a networked or within a client-server envi-ronment, etc.

According to the depicted embodiment, the system 701, includes the processor 790 and the memory 795 to execute instructions at the system 701. The system 701 as depicted here is specifically customized and configured to perform self-supervised visual representation learning using order and appearance recovery on a vision transformer, in which trained models may then be utilized for the processing of medical imaging.

According to a particular embodiment, system 701 is specially configured to execute instructions for performing self-supervised visual representation learning using order and appearance recovery on a vision transformer, by per-forming operations including: receiving one or more medi-cal images 740 as training data input at the system 701; selecting a medical image from among the training data input 740 for use with performing the self-supervised visual representation learning via the system 701 using the base ViT model 739 or a non-default user-specified ViT model 727. The system 701 generates a patchified image 729A (e.g., a perturbed image having been broken into multiple "patches" or exposed to other perturbations) from the medical image selected by applying local pixel shuffling (e.g., via the image perturbations module 791) to the medical image 740 to generate a shuffled image, applying one or more additional image perturbations (e.g., via the image perturbations module 791) to the shuffled image, to generate an interim perturbed image, transforming the interim perturbed image into a first group of patches (e.g., via the image patchification generator 750), in which the first group of patches collectively corresponds to the interim perturbed image. The system then outputs the first group of patches as the first perturbed or patchified image 729A which is provided as input into the first transformer encoder 255A. The system 701 additionally generates a second perturbed image 729B from the medical image selected by transforming the medical image selected into a second group of patches collectively corresponding to the medical image selected (e.g., via the image patchification generator 750), and by next applying a random permutation to the second group of patches to generate a patch randomized interim image, and outputting the patch randomized interim image as the second perturbed image or the randomized patch image 729B which is provided as input into the second transformer encoder 255B.

The system thus inputs the first perturbed image 729A into a first transformer encoder 255A to generate a first set of weights 256A through the recovery of both and patch order appearance from the first perturbed image and further inputs the second perturbed image 729B into a second transformer encoder 255B, different than the first transformer encoder 255A, to generate a second set of weights 256B through the recovery of both and patch order appearance from the second perturbed image. The first and second sets of weights derived from the vision based SSL learning at the ViT or and appearance recovery platform 745 of the system 701 are then shared between the first and second transformer encoders.

The system then outputs a pre-trained AI model 742 to perform medical image diagnosis on a new medical image which forms no part of the training data input received by the system. The system may optionally fine-tune the pre-trained AI model to generate the fine-tuned AI model 743 subsequent to pre-training.

Bus 714 interfaces the various components of the system 701 amongst each other, with any other peripheral(s) of the system 701 such as the database system storage 746, and with external components such as external network elements, other machines, client devices, cloud computing services, etc. Communications may further include communicating with external devices via a network interface over a LAN, WAN, or the public Internet.

Figure 8:
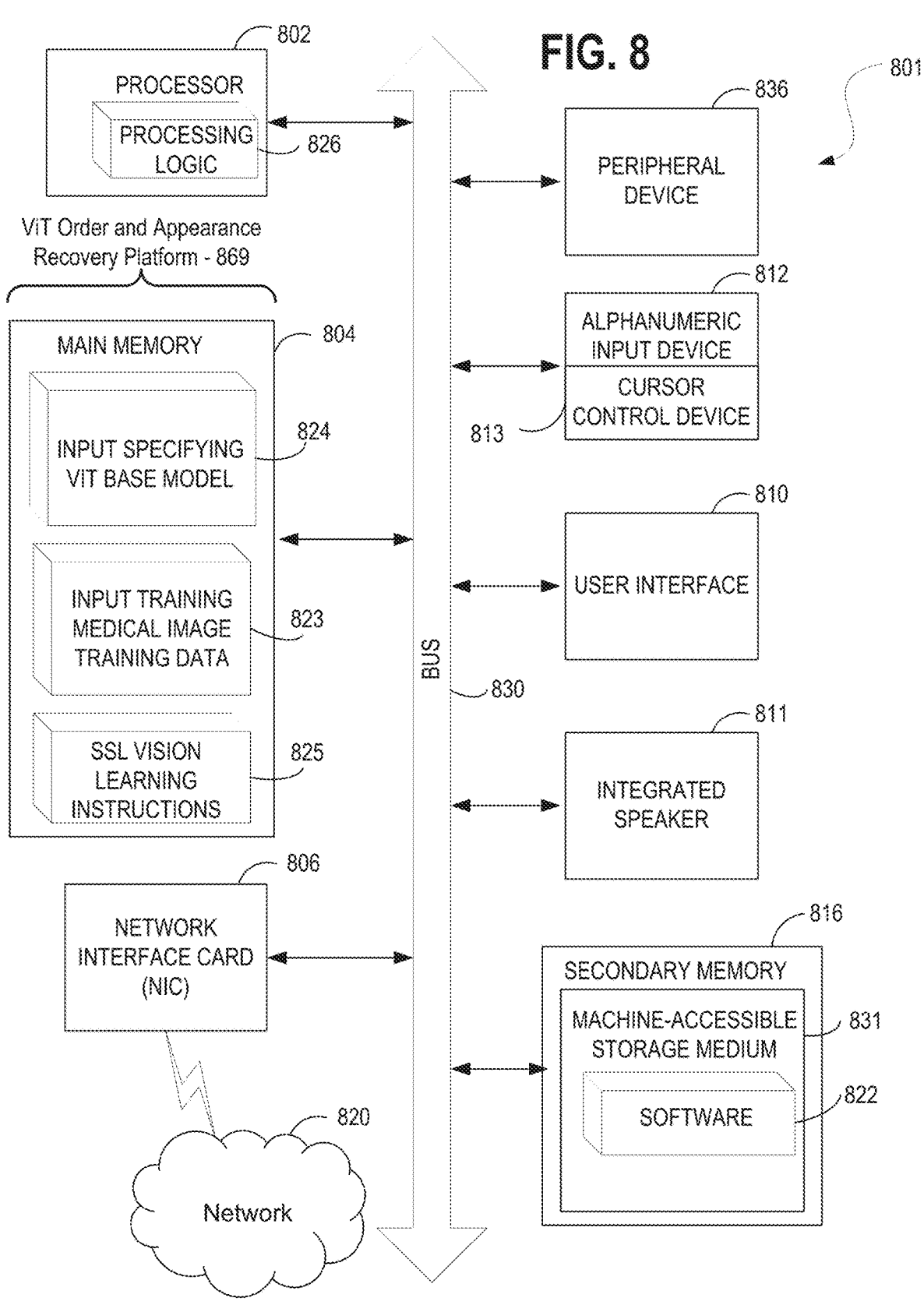
FIG. 8 illustrates a diagrammatic representation of a machine in the exemplary form of a computer system, in accordance with one embodiment.

FIG. 8 illustrates a diagrammatic representation of a machine 801 in the exemplary form of a computer system, in accordance with one embodiment, within which a set of instructions, for causing the machine/computer system to perform any one or more of the methodologies discussed herein, may be executed.

In alternative embodiments, the machine may be connected (e.g., networked) to other machines in a Local Area Network (LAN), an intranet, an extranet, or the public Internet. The machine may operate in the capacity of a server or a client machine in a client-server network environment, or as a peer machine in a peer-to-peer (or distributed) network environment, as a server or series of servers within an on-demand service environment. Certain embodiments of the machine may be in the form of a personal computer (PC), a tablet PC, a set-top box (STB), a Personal Digital Assistant (PDA), a cellular telephone, a web appliance, a server, a network router, switch or bridge, computing system, or any machine capable of executing a set of instructions (sequential or otherwise) that specify and mandate the specifically configured actions to be taken by that machine pursuant to stored instructions. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary machine 801 includes a processor 802, a main memory 804 (e.g., read-only memory (ROM), flash memory, dynamic random access memory (DRAM) such as synchronous DRAM (SDRAM) or Rambus DRAM (RDRAM), etc., static memory such as flash memory, static random access memory (SRAM), volatile but high-data rate RAM, etc.), and a secondary memory 816 (e.g., a persistent storage device including hard disk drives and a persistent database and/or a multi-tenant database implementation), which communicate with each other via a bus 830. Main memory 804 includes instructions for executing the various benchmarking techniques of the ViT Order and Appearance Recovery Platform 869 as described herein, including the execution components configured for receiving input specifying a ViT base model 824, configured for receiving the input training medical image training data 823, and execution components configured for generating and outputting a pre-trained AI model and optionally a pre-trained and fine-tuned AI model. Further depicted are the SSL vision learning instructions 825 which are applied to using a default or user specified base ViT model, in support of the methodologies and techniques described herein. Main memory 804 and its sub-elements are further operable in conjunction with processing logic 826 and processor 802 to perform the methodologies discussed herein.

Processor 802 represents one or more specialized and specifically configured processing devices such as a microprocessor, central processing unit, or the like. More particularly, the processor 802 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 802 may also be one or more special-purpose processing devices such as an application-specific integrated circuit (ASIC), a field programmable gate array (FPGA), a digital signal processor (DSP), network processor, or the like. Processor 802 is configured to execute the processing logic 826 for performing the operations and functionality which is discussed herein.

The machine 801 may further include a network interface card 806. The machine 801 also may include a user interface 810 (such as a video display unit, a liquid crystal display, etc.), an alphanumeric input device 812 (e.g., a keyboard), a cursor control device 813 (e.g., a mouse), and a signal generation device 811 (e.g., an integrated speaker). The machine 801 or computer system may further include peripheral device 836 (e.g., wireless or wired communication devices, memory devices, storage devices, audio processing devices, video processing devices, etc.).

The secondary memory 816 may include a non-transitory machine-readable storage medium or a non-transitory computer readable storage medium or a non-transitory machine-accessible storage medium 831 on which is stored one or more sets of instructions (e.g., software 822) embodying any one or more of the methodologies or functions described herein. The software 822 may also reside, completely or at least partially, within the main memory 804 and/or within the processor 802 during execution thereof by the machine 801, the main memory 804 and the processor 802 also constituting machine-readable storage media. The software 822 may further be transmitted or received over a network 820 via the network interface card 806.

While the subject matter disclosed herein has been described by way of example and in terms of the specific embodiments, it is to be understood that the claimed embodiments are not limited to the explicitly enumerated embodiments disclosed. To the contrary, the disclosure is intended to cover various modifications and similar arrangements as are apparent to those skilled in the art. Therefore, the scope of the appended claims is to be accorded the broadest interpretation so as to encompass all such modifications and similar arrangements. It is to be understood that the above description is intended to be illustrative, and not restrictive. Many other embodiments will be apparent to those of skill in the art upon reading and understanding the above description. The scope of the disclosed subject matter is therefore to be determined in reference to the appended claims, along with the full scope of equivalents to which such claims are entitled.

What is claimed is:

1. A system comprising:

a memory to store instructions;

a processor to execute the instructions stored in the memory, including:

receiving one or more medical images as training data input at the system;

selecting a medical image from among the training data;

generating a first perturbed image from the medical image selected by applying local pixel shuffling to the medical image to generate a shuffled image, applying one or more additional image perturbations to the shuffled image, to generate an interim perturbed image, transforming the interim perturbed image into a first group of patches collectively corresponding to the interim perturbed image, and outputting the first group of patches as the first perturbed image;

generating a second perturbed image from the medical image selected by transforming the medical image selected into a second group of patches collectively corresponding to the medical image selected, applying a random permutation to the second group of patches to generate a patch randomized interim image, and outputting the patch randomized interim image as the second perturbed image;

inputting the first perturbed image into a first transformer encoder to perform self-supervised visual representation learning by recovering order and appearance information from the first perturbed image, resulting in a first set of weights associated with the first perturbed image;

inputting the second perturbed image into a second transformer encoder, different than the first transformer encoder, to perform self-supervised visual representation learning by recovering order and appearance information from the second perturbed image, resulting in a second set of weights associated with the second perturbed image;

sharing the first and second sets of weights among the first and second transformer encoders; and outputting a pre-trained AI model to perform medical image diagnosis on a new medical image which forms no part of the training data input received by the system.

2. The system of claim 1, further comprising:

applying fine-tuning to the pre-trained AI model using a publicly available standardized dataset; and outputting the pre-trained and fined-tuned AI model to perform the medical image diagnosis.

3. The system of claim 2, wherein:

applying the fine-tuning to the pre-trained AI model using the publicly available standardized dataset comprises using one of a publicly available standardized NIH ChestX-ray14 dataset or a publicly available standardized CheXpert dataset.

4. The system of claim 1:

wherein applying the one or more additional image perturbations to the shuffled image comprises:

applying non-linear processing to the shuffled image to generate a processed shuffled image;

applying in-painting or out-painting or both in-painting and out-painting to the processed shuffled image to generate an expanded image; and wherein transforming the interim perturbed image into the first group of patches collectively corresponding to the interim perturbed image comprises transforming the expanded image into the first group of patches collectively corresponding to the expanded image generated from the application of the in-painting or out-painting or both.

5. The system of claim 1:

wherein a Vision Transformer (ViT) base model is utilized as a default backbone for applying the first and second image perturbations of the medical image.

6. The system of claim 1:

wherein a user-specified Vision Transformer (ViT) model is specified as a second input;

supplementing a Vision Transformer (ViT) base model utilized as a default backbone with the user-specified Vision Transformer (ViT) model specified as the second input; and applying the first and second image perturbations of the medical image utilizing the user-specified Vision Transformer (ViT) model as specified via the second input.

7. The system of claim 1:

wherein applying the local pixel shuffling to the medical image to generate the shuffled image comprises applying the local pixel shuffling at a 50% application threshold to generate the shuffled image.

8. The system of claim 1:

wherein transforming the interim perturbed image into a first group of patches collectively corresponding to the interim perturbed image, and outputting the first group of patches as the first perturbed image comprises executing instructions via the processor for applying a patchify algorithm to the interim perturbed image to generate the first perturbed image.

9. The system of claim 1:

wherein transforming the interim perturbed image into a first group of patches collectively corresponding to the interim perturbed image comprises, dividing the interim perturbed image into a 4×4 block of 16 total patches or into an 8×8 block of 64 total patches; and outputting the 4×4 block of 16 total patches or the 8×8 block of 64 total patches as the first perturbed image.

15

16

10. The system of claim 1:

wherein generating the first perturbed image from the medical image and generating the second perturbed image from the medical image comprises executing a Vision Transformer (ViT) at the system against the medical image selected to generate the first and second perturbed images.

11. A computer-implemented method performed by a system having at least a processor and a memory therein to execute instructions comprising:

receiving one or more medical images as training data input at the system;

selecting a medical image from among the training data;

generating a first perturbed image from the medical image selected by applying local pixel shuffling to the medical image to generate a shuffled image, applying one or more additional image perturbations to the shuffled image, to generate an interim perturbed image, transforming the interim perturbed image into a first group of patches collectively corresponding to the interim perturbed image, and outputting the first group of patches as the first perturbed image;

generating a second perturbed image from the medical image selected by transforming the medical image selected into a second group of patches collectively corresponding to the medical image selected, applying a random permutation to the second group of patches to generate a patch randomized interim image, and outputting the patch randomized interim image as the second perturbed image;

inputting the first perturbed image into a first transformer encoder to perform self-supervised visual representation learning by recovering order and appearance information from the first perturbed image, resulting in a first set of weights associated with the first perturbed image;

inputting the second perturbed image into a second transformer encoder, different than the first transformer encoder, to perform self-supervised visual representation learning by recovering order and appearance information from the second perturbed image, resulting in a second set of weights associated with the second perturbed image;

sharing the first and second sets of weights among the first and second transformer encoders; and outputting a pre-trained AI model to perform medical image diagnosis on a new medical image which forms no part of the training data input received by the system.

12. The computer-implemented method of claim 11, further comprising:

applying fine-tuning to the pre-trained AI model using a publicly available standardized dataset;

outputting the pre-trained and fined-tuned AI model to perform the medical image diagnosis; and wherein the publicly available standardized dataset comprises one of a publicly available standardized NIH ChestX-ray14 dataset or a publicly available standardized CheXpert dataset.

13. The computer-implemented method of claim 11:

wherein applying the one or more additional image perturbations to the shuffled image comprises:

applying non-linear processing to the shuffled image to generate a processed shuffled image;

applying in-painting or out-painting or both in-painting and out-painting to the processed shuffled image to generate an expanded image; and wherein transforming the interim perturbed image into the first group of patches collectively corresponding to the interim perturbed image comprises transforming the expanded image into the first group of patches collectively corresponding to the expanded image generated from the application of the in-painting or out-painting or both.

14. The computer-implemented method of claim 11:

wherein a Vision Transformer (ViT) base model is utilized as a default backbone for applying the first and second image perturbations of the medical image.

15. The computer-implemented method of claim 11:

wherein a user-specified Vision Transformer (ViT) model is specified as a second input;

supplementing a Vision Transformer (ViT) base model utilized as a default backbone with the user-specified Vision Transformer (ViT) model specified as the second input; and applying the first and second image perturbations of the medical image utilizing the user-specified Vision Transformer (ViT) model as specified via the second input.

16. The computer-implemented method of claim 11:

wherein applying the local pixel shuffling to the medical image to generate the shuffled image comprises applying the local pixel shuffling at a 50% application threshold to generate the shuffled image.

17. The computer-implemented method of claim 11:

wherein transforming the interim perturbed image into a first group of patches collectively corresponding to the interim perturbed image, and outputting the first group of patches as the first perturbed image comprises executing instructions via the processor for applying a patchify algorithm to the interim perturbed image to generate the first perturbed image.

18. The computer-implemented method of claim 11:

wherein transforming the interim perturbed image into a first group of patches collectively corresponding to the interim perturbed image comprises, dividing the interim perturbed image into a 4×4 block of 16 total patches or into an 8×8 block of 64 total patches; and outputting the 4×4 block of 16 total patches or the 8×8 block of 64 total patches as the first perturbed image.

19. The computer-implemented method of claim 11:

wherein generating the first perturbed image from the medical image and generating the second perturbed image from the medical image comprises executing a Vision Transformer (ViT) at the system against the medical image selected to generate the first and second perturbed images.

20. Non-transitory computer readable storage media having instructions stored thereupon that, when executed by a system having at least a processor and a memory therein, the instructions cause the processor to execute instructions, including:

receiving one or more medical images as training data input at the system;

selecting a medical image from among the training data;

generating a first perturbed image from the medical image selected by applying local pixel shuffling to the medical image to generate a shuffled image, applying one or more additional image perturbations to the shuffled image, to generate an interim perturbed image, transforming the interim perturbed image into a first group of patches collectively corresponding to the interim perturbed image, and outputting the first group of patches as the first perturbed image;

generating a second perturbed image from the medical
image selected by transforming the medical image
selected into a second group of patches collectively
corresponding to the medical image selected, applying
a random permutation to the second group of patches to
generate a patch randomized interim image, and out-
putting the patch randomized interim image as the
second perturbed image;
inputting the first perturbed image into a first transformer
encoder to perform self-supervised visual representation learning by recovering order and appearance infor-
mation from the first perturbed image, resulting in a
first set of weights associated with the first perturbed
image;
inputting the second perturbed image into a second transformer encoder, different than the first transformer
encoder, to perform self-supervised visual representa-
tion learning by recovering order and appearance infor-
mation from the first perturbed image, resulting in a
second set of weights associated with the second perturbed image;
sharing the first and second sets of weights among the first
and second transformer encoders; and
outputting a pre-trained AI model to perform medical
image diagnosis on a new medical image which forms
no part of the training data input received by the
system.

* * * * *